(12) United States Patent
Hu et al.

(10) Patent No.: US 11,925,559 B2
(45) Date of Patent: Mar. 12, 2024

(54) METHOD FOR IN VITRO SIMULATION AND EVALUATION OF PLATELET ADHESION IN BLOOD-CONTACTING MEDICAL DEVICES

(71) Applicant: FUWAI HOSPITAL CHINESE ACADEMY OF MEDICAL SCIENCES, SHENZHEN, Shenzhen (CN)

(72) Inventors: Shengshou Hu, Beijing (CN); Guangmao Liu, Beijing (CN)

(73) Assignee: FUWAI HOSPITAL CHINESE ACADEMY OF MEDICAL SCIENCES, SHENZHEN, Shenzhen (CN)

( * ) Notice: Subject to any disclaimer, the term of this patent is extended or adjusted under 35 U.S.C. 154(b) by 619 days.

(21) Appl. No.: 17/275,203

(22) PCT Filed: May 21, 2020

(86) PCT No.: PCT/CN2020/091505
§ 371 (c)(1),
(2) Date: Mar. 11, 2021

(87) PCT Pub. No.: WO2021/077732
PCT Pub. Date: Apr. 29, 2021

(65) Prior Publication Data
US 2022/0015907 A1    Jan. 20, 2022

(30) Foreign Application Priority Data
Oct. 24, 2019    (CN) .......................... 201911021299.8

(51) Int. Cl.
*A61F 2/24*        (2006.01)
*A61F 2/82*        (2013.01)
*A61M 60/117*      (2021.01)
*G01N 15/06*       (2006.01)
*G01N 33/49*       (2006.01)

(52) U.S. Cl.
CPC .............. *A61F 2/2472* (2013.01); *A61F 2/82* (2013.01); *A61M 60/117* (2021.01);
(Continued)

(58) Field of Classification Search
CPC ....... A61F 2/2472; A61F 2/82; A61M 60/117; G01N 15/0606; G01N 15/075; G01N 2015/018; G01N 33/4905
See application file for complete search history.

(56) References Cited

FOREIGN PATENT DOCUMENTS

| CN | 101251434 A | 8/2008 |
|---|---|---|
| CN | 101347360 A | 1/2009 |

(Continued)

OTHER PUBLICATIONS

English Machine Translation of CN109900885A. (Year: 2019).*
(Continued)

*Primary Examiner* — Jennifer Wecker
*Assistant Examiner* — Kathryn Elizabeth Limbaugh
(74) *Attorney, Agent, or Firm* — Bayramoglu Law Offices LLC

(57) ABSTRACT

A method for in vitro simulation and evaluation of platelet adhesion in blood-contacting medical devices is disclosed, including the following steps: (1) using a glycerin aqueous solution with a mass percentage concentration of 40% in an extracorporeal circulation circuit to simulate a viscosity and hydrodynamic characteristics of blood, and adding fluorescent particles with a diameter of 3 μm to 5 μm to the solution to simulate platelets; (2) after the solution circulates in the circuit for a specified time period, removing flow passage components of a tested device, and observing the deposition of the fluorescent particles on a blood-contacting surface inside the device by naked eyes and photographs; and (3) using laser-induced fluorescence (LIF) technique to apply laser light on a device surface deposited with the fluorescent
(Continued)

particles and in contact with blood, and using charge-coupled device (CCD) camera imaging to photograph the aggregation and adhesion of laser-induced fluorescent particles.

5 Claims, 8 Drawing Sheets

(52) U.S. Cl.
CPC ... *G01N 15/0606* (2013.01); *G01N 2015/018* (2024.01); *G01N 15/075* (2024.01); *G01N 33/4905* (2013.01)

(56) References Cited

FOREIGN PATENT DOCUMENTS

| | | | |
|---|---|---|---|
| CN | 101361988 | A | 2/2009 |
| CN | 109900885 | A | 6/2019 |
| WO | 0066730 | A2 | 11/2000 |

OTHER PUBLICATIONS

Fallon et al., "Procoagulant Properties of Flow Fields in Stenotic and Expansive Orifices", Nov. 6, 2007, Annals of Biomedical Engineering, vol. 36, pp. 1-13. (Year: 2007).*

Manning et al., "Flow Through an Outlet Cannula of a Rotary Ventricular Assist Device", 2002, Artif Organs, vol. 26, 714-723. (Year: 2002).*

Guang-Mao Liu, et al., Platelet adhesion emulation: A novel method for estimating the device thrombosis potential of a ventricular assist device, The International Journal of Artificial Organs, 2020, pp. 252-257, vol. 43 No. 4, Sage.

Mingzhi Bing, Impact of vena cava filter implantation on inferior vena cava and the Particle image velocimetry (PIV) test on Flow-Field after implantation, 2015, 100 pages.

* cited by examiner

METHOD FOR IN VITRO SIMULATION AND EVALUATION OF PLATELET ADHESION IN BLOOD-CONTACTING MEDICAL DEVICES

CROSS REFERENCE TO THE RELATED APPLICATIONS

This application is the national phase entry of International Application No. PCT/CN2020/091505, filed on May 21, 2020, which is based upon and claims priority to Chinese Patent Application No. 201911021299.8, filed on Oct. 24, 2019, the entire contents of which are incorporated herein by reference.

TECHNICAL FIELD

The present invention belongs to the technical field of testing and evaluating blood-contacting medical devices, and particularly relates to a method for in vitro simulation and evaluation of platelet adhesion in blood-contacting medical devices.

BACKGROUND

There are many challenges in the development of blood-contacting medical devices (such as vascular stents, mechanical valves, and artificial hearts). When blood flows through blood-contacting medical devices, due to flow factors such as non-physiological blood flow shear stress, low-speed flow, and flow stagnation and non-autologous mechanical structure factors, platelets often adhere to the surface of these devices until a series of problems such as thrombosis occur, thereby limiting the clinical application of blood-contacting medical devices. A platelet adhesion and thrombosis location in blood-contacting medical devices is bound up with a structure of the location. Taking artificial hearts as an example, in artificial hearts that have been clinically used, thrombosis in pumps has always been one of adverse events (AEs), and almost all thrombosis events in artificial hearts occur at several fixed locations inside artificial hearts. Research has found that platelet activation is universal and globally recorded in artificial hearts. Platelets, after being activated and aggregating in large amounts, do not necessarily adhere to an artificial heart to form thrombi, so platelet adhesion and thrombosis in artificial hearts are probabilistic and local.

Structures of flow passage components of a blood-contacting medical device determine the flow field and flow distribution of blood flow in the device, and eddy current, high shear stress, stagnant flow, etc. will cause thrombosis in the device. At present, in a process of designing and testing blood-contacting medical devices, there is a lack of intuitive and effective methods to evaluate the defect of thrombosis due to platelet adhesion on a surface inside a device that is in contact with blood. Currently, location and incidence of thrombosis in blood-contacting medical devices are counted basically through large-scale animal experiments and clinical trials. That is, the numerical calculation and flow field visualization methods are first used to obtain blood flow conditions in a device, then the blood flow conditions are analyzed to determine whether platelet adhesion is likely to occur in the device, and thrombosis and high-incidence locations thereof caused by platelet adhesion in the device are counted through a large number of expensive animal experiments and clinical trials, which requires numerous labor and material resources to discover deficiencies of a device design.

Therefore, counting location and incidence of thrombosis in a blood-contacting medical device through large-scale animal experiments and clinical trials not only requires a long testing period and a high cost, but also leads to a lengthy optimization and improvement period for the device. Moreover, obtaining statistical data of deficiencies through clinical trials fails to take maximum responsibility for patients.

SUMMARY

The present invention is intended to provide a method for in vitro simulation and evaluation of platelet adhesion caused by structural deficiencies or flow factors on a blood-contacting surface in blood-contacting medical devices. Through the new method, a location where platelet adhesion and thrombi are likely to form in a device can be located to analyze structural deficiencies of the location and improve and optimize in time. With this method, deficiencies in the device and whether the deficiencies can be further improved can be determined before clinical applications.

To achieve the above objective, the present invention adopts the following technical solutions:

A method for in vitro simulation and evaluation of platelet adhesion in a blood-contacting medical device, including the following steps:

(1) using a glycerin aqueous solution with a mass percentage concentration of 40% in an extracorporeal circulation circuit to simulate a viscosity and hydrodynamic characteristics of blood, and adding fluorescent particles with a diameter of 3 μm to 5 μm to the solution to simulate platelets;

(2) after the solution circulates in the circuit for 24 h, removing flow passage components of a tested device, and observing the deposition of the fluorescent particles on a blood-contacting surface inside the device by naked eyes and photographs; and (3) using a laser-induced fluorescence (LIF) technique to apply laser light on a device surface deposited with the fluorescent particles and in contact with blood, and using a charge-coupled device (CCD) camera imaging method to photograph the aggregation and adhesion of laser-induced fluorescent particles.

In the step (1), the fluorescent particles may have a volume percentage concentration ranging from 5% to 30% in the solution.

In the method, if the deposition of the fluorescent particles does not occur after 3 days of the experiment, the tested device is removed, and the device is determined to have no structural deficiencies that can lead to significant platelet adhesion.

The artificial organ or medical device may be an artificial heart, a vascular stent, a mechanical valve, or the like. For non-powered devices such as the vascular stent and the mechanical valve, a traditional rotary pump may be used to achieve the flow of the solution in the circulation circuit; and for powered devices such as the artificial heart, the circulation flow of the solution in the circulation circuit is achieved directly relying on their own power.

The present invention has the following advantages.

The method of the present invention adopts the laser-induced fluorescent particle deposition effect to simulate platelet adhesion on an inner surface of a blood-contacting medical device in vitro, which can not only locate locations and structural characteristics of platelet adhesion and thrombi easily formed in the device, but also complement a missed in vitro test link between the numerical models and animal experiments for platelet adhesion and thrombosis. This method can be used to predict the platelet adhesion in the device and evaluate a platelet adhesion and thrombosis risk of a specified local structure inside the device. The method can guide the structural optimization and improvement of a device at a design and optimization stage of the device and can also serve as a method for evaluating the hemocompatibility of a device at a registration test stage of the device, which can greatly reduce the development cycle and cost of such devices.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

The present invention will be further illustrated below through examples, but the protection scope of the present invention is not limited by these examples.

Figure 1:
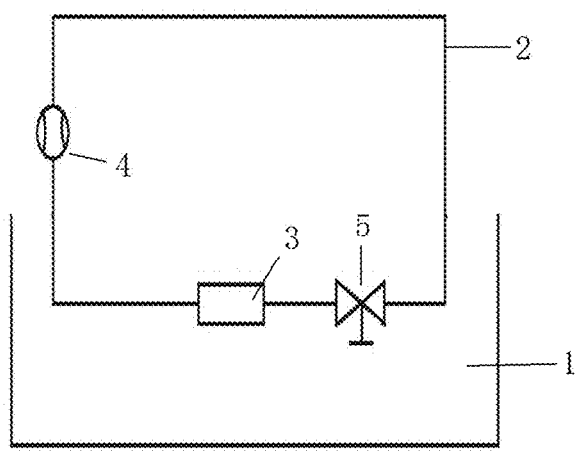
FIG. 1 is a schematic diagram showing a structure of the circulation circuit used in the present invention.

As shown in FIG. 1, the method of the present invention adopts a circulation circuit composed of the liquid storage tank 1 and the silica gel pipeline 2. The silica gel pipeline 2 is provided with the artificial organ or medical device 3, the flow meter 4, and the valve 5, and the rotary pump for providing power is disposed as needed. The liquid storage tank 1 is filled with a solution that simulates human blood, and the artificial organ or medical device 3 is placed in the solution. The present invention adopts a glycerin aqueous solution with a concentration of 40% as a circulating medium.

The experimental method of the present invention is as follows. A blood-contacting medical device is connected to the extracorporeal circulation circuit, and then fluorescent particles with a diameter of 3 μm to 5 μm are added to the solution to simulate platelets. The fluorescent particles have a concentration ranging from 5% to 30% in the solution. For non-powered devices such as a vascular stent and a mechanical valve, a traditional rotary pump may be used to achieve the flow of the solution in the circulation circuit; and for powered devices such as an artificial heart, the flow of the solution in the circulation circuit is achieved directly relying on their own power. After the solution circulates in the circuit for a specified time period, the deposition of fluorescent particles on a blood-contacting surface is observed. If there is significant deposition, flow passage components in the tested device are removed to observe the fluorescent particle deposition on the blood-contacting surface in the device by naked eyes and photographs. Then the LIF technique is used to apply laser light on the surface of the device that is in contact with blood and deposited with the fluorescent particles, and the aggregation and adhesion of fluorescent particles are observed in the CCD camera imaging through laser-induced fluorescent particles. If no fluorescent particle deposition occurs, the tested device is removed after the experiment is conducted for 3 days, and it is determined that there are no structural deficiencies in the device that can lead to significant platelet adhesion.

When blood-contacting medical devices are used in clinics, platelet adhesion occurs due to flow factors in the human body resulting from some structures of the devices. The method of the present invention can be used to locate a location and a structure in a device where platelet adhesion is most likely to occur. Therefore, the method can be used to guide the structural improvement of the device and can also be used for the registration test of the device's performance evaluation before the device goes on the market. The present invention provides a guiding method for analyzing which local structural deficiencies in the device will cause platelet adhesion and thrombosis, which is of great significance for the development of blood-contacting medical devices.

Example

Figure 2:
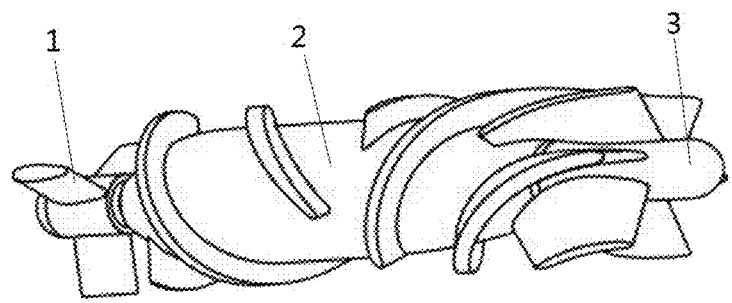
FIG. 2 is a schematic diagram showing a structure of the type III axial flow blood pump model used in the example.

Taking an artificial heart as an example, a simulated blood flow experiment is conducted on the type III axial flow blood pump model to evaluate the particle deposition and adhesion on the surfaces of a stator, a rotor, and a shell in the blood pump model. As shown in FIG. 2, the type III axial flow blood pump model used in this example is composed of three parts: the front guide 1, the rotor 2, and the rear guide 3.

The devices and materials used in the experiment are shown in the table below.

| | |
|---|---|
| CCD camera | B5M16 resolution: 2456*2058, acquisition rate: 1-8 HZ |
| Lens | NIKON 50 mm 1:1.4D |
| Laser device | model: Vlite-200 double-pulse laser, wavelength: 532 nm; single-pulse energy: 200 mJ; repetitive working frequency: 1-15 Hz |
| Circulating water pump | rated power circulating water pump |
| Tracer particles | fluorescent powder (magnesium arsenate, density: 1.34 g/cm$^3$, average particle size: 5 μm) |
| Workstation | HpZ440, Intel(R) Xeon(R) CPU E5-1620 v4 @ 3.50 GHz |
| Blood pump | type III axial flow blood pump |
| Color filter | dedicated high-pass color filter, center wavelength: 560 nm |
| Glycerin | 1,2,3-propanetriol |

Experimental process is as follows. 1) Glycerin and water are mixed at a concentration ratio of 4:6 to prepare a solution to simulate a blood viscosity. 2) The fluorescent powder is added to the prepared solution at a volume proportion of 20%, and a resulting mixture is thoroughly stirred until particles are evenly distributed. 3) The circulating water pump and blood pump model are connected, and then it is electrified to make the solution fully circulate. In the solution, the pump rotor is driven by the circulating water pump to rotate. 4) The circulating water pump drives the solution to flow through the blood pump, and particles will deposit on a model wall surface and the surfaces of the stator and rotor. 5) After the solution is circulated in the circuit for 24 h, the flow passage components of the tested device are removed to observe the deposition of the fluorescent particles on a blood-contacting surface inside the device by naked eyes and photographs. 6) In order to display the deposition effects on the wall surface of the model and the surfaces of the stator and rotor, the LIF method is used to irradiate the surface of the model with laser light, and the deposition effect of particles on the surface of the model is photographed. The fluorescent particles attached to the surface are induced by the laser light to produce light with a specific wavelength and thus imaged through the fluorescent color filter on the CCD camera, thereby observing the liquid adhesion on the rotor surface.

Figure 3:
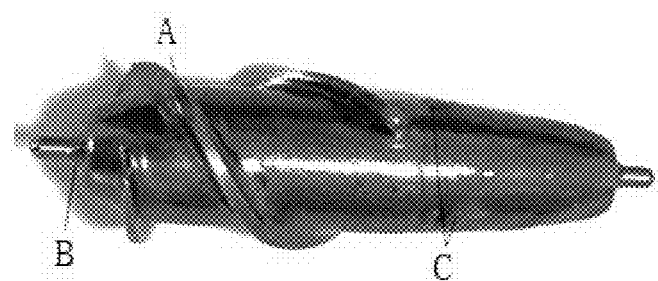
FIG. 3 is a diagram illustrating the particle adhesion effect on a component surface observed through photographing after the experiment.
Figure 4A:
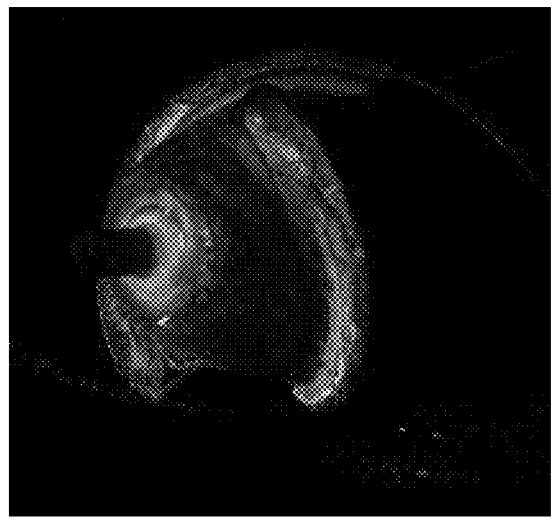
FIG. 4A is a diagram showing the particle adhesion effect on the surface of a rotor at a first angle after laser induction.
Figure 4B:
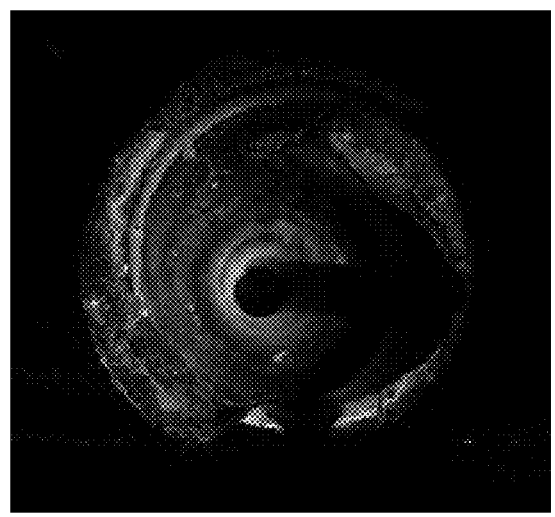
FIG. 4B is a diagram showing the particle adhesion effect on the surface of the rotor at a second angle after laser induction.
Figure 4C:
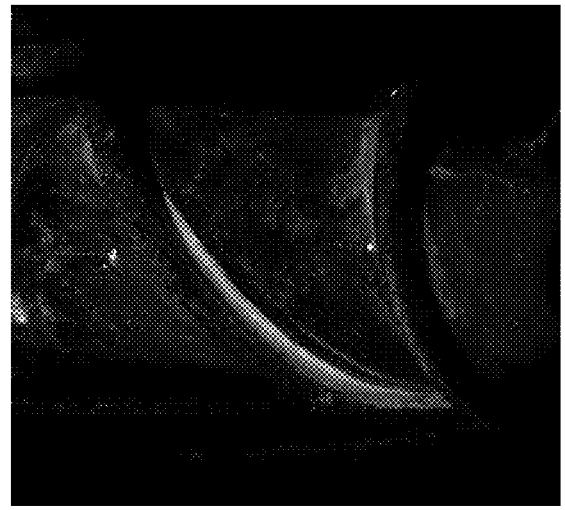
FIG. 4C is a diagram showing the particle adhesion effect on the surface of the rotor at a third angle after laser induction.
Figure 4D:
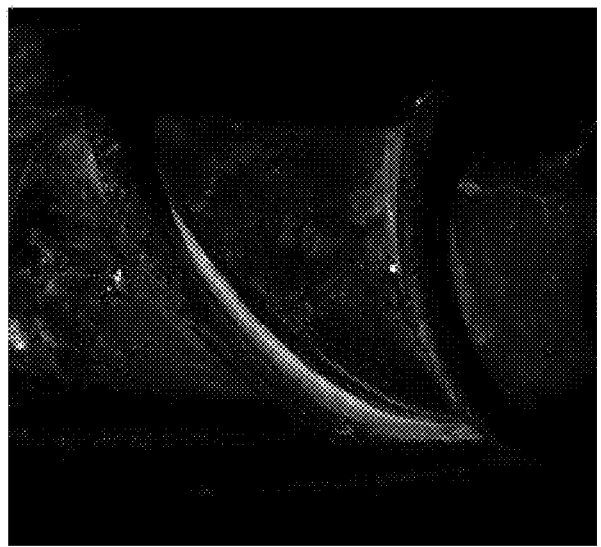
FIG. 4D is a diagram showing the particle adhesion effect on the surface of the rotor at a fourth angle after laser induction.
Figure 4E:
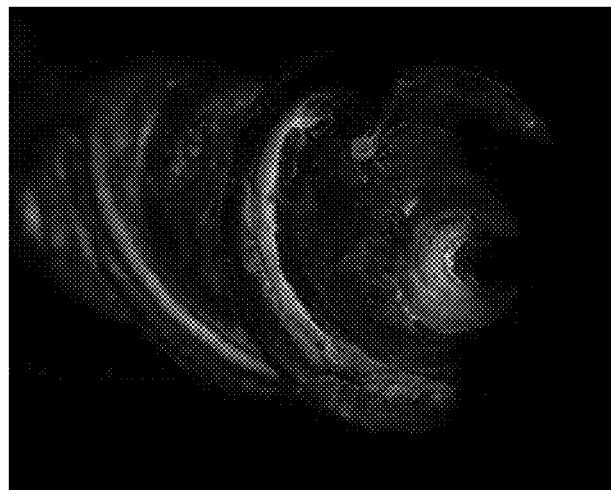
FIG. 4E is a diagram showing the particle adhesion effect on the surface of the rotor at a fifth angle after laser induction.
Figure 4F:
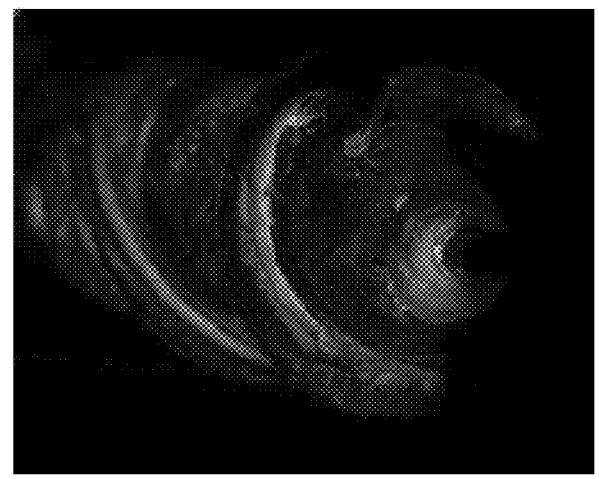
FIG. 4F is a diagram showing the particle adhesion effect on the surface of the rotor at a sixth angle after laser induction.
Figure 5A:
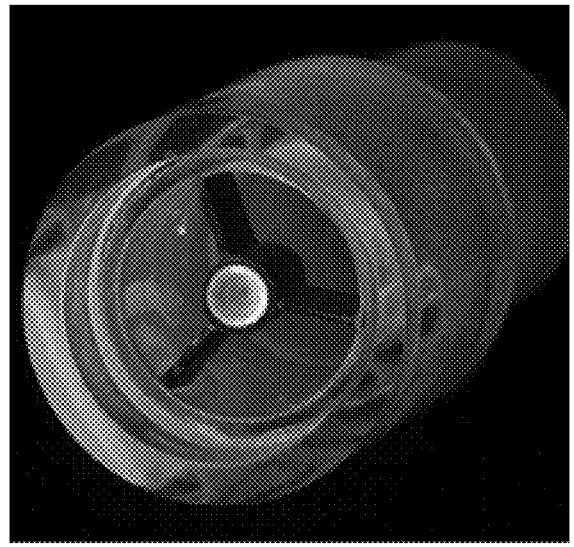
FIG. 5A is a diagram showing the particle adhesion effect on the surface of a stator in an inlet section at a first angle after laser induction.
Figure 5B:
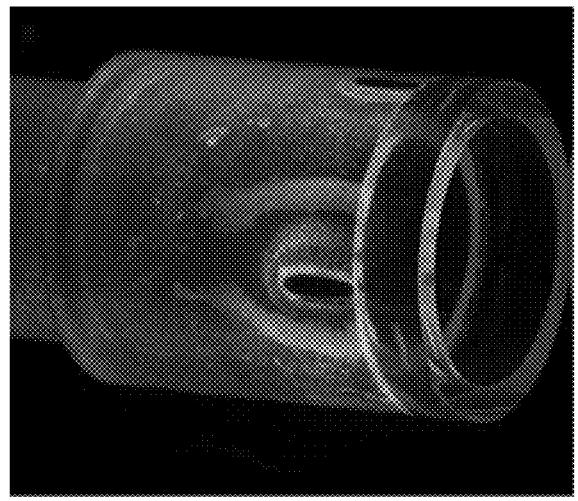
FIG. 5B is a diagram showing the particle adhesion effect on the surface of the stator in the inlet section at a second angle after laser induction.
Figure 5C:
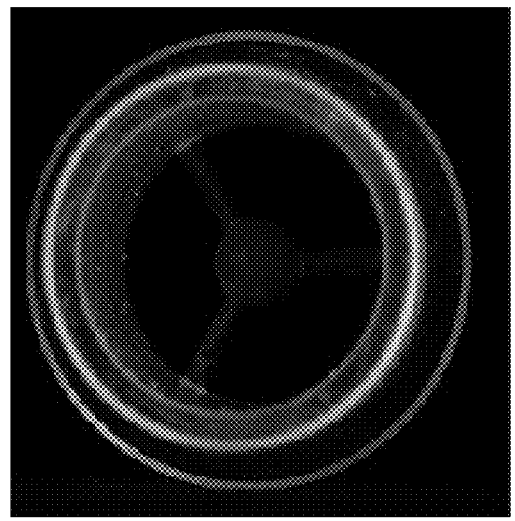
FIG. 5C is a diagram showing the particle adhesion effect on the surface of the stator in the inlet section at a third angle after laser induction.
Figure 5D:
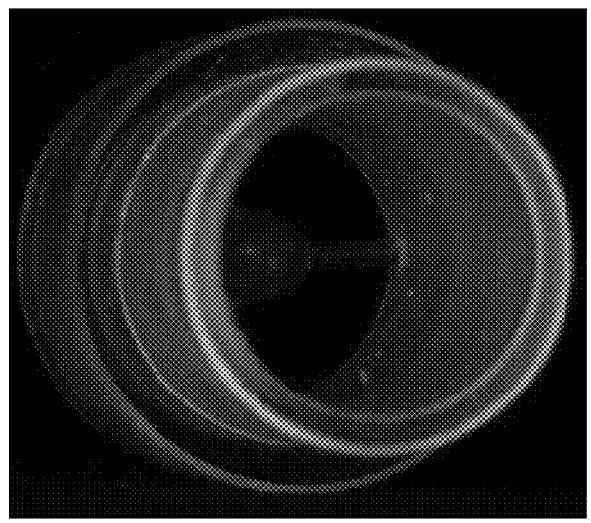
FIG. 5D is a diagram showing the particle adhesion effect on the surface of the stator in the inlet section at a fourth angle after laser induction.
Figure 6A:
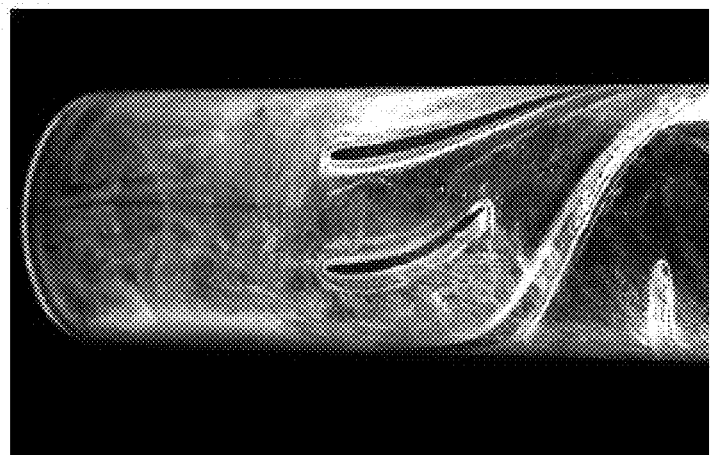
FIG. 6A is a diagram showing the particle adhesion effect on the surfaces of a stator and a wall in an outlet section at a first angle after laser induction.
Figure 6B:
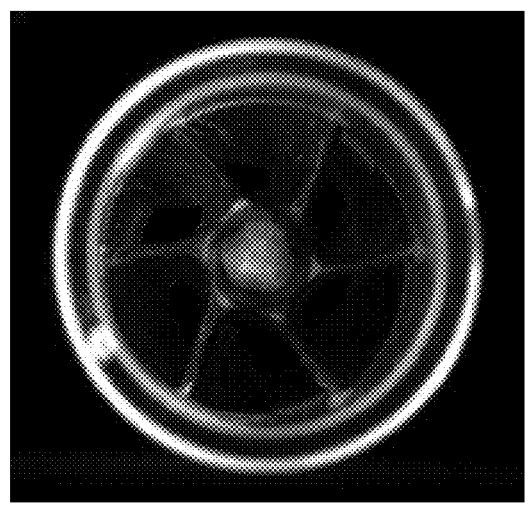
FIG. 6B is a diagram showing the particle adhesion effect on the surfaces of the stator and the wall in the outlet section at a second angle after laser induction.
Figure 6C:
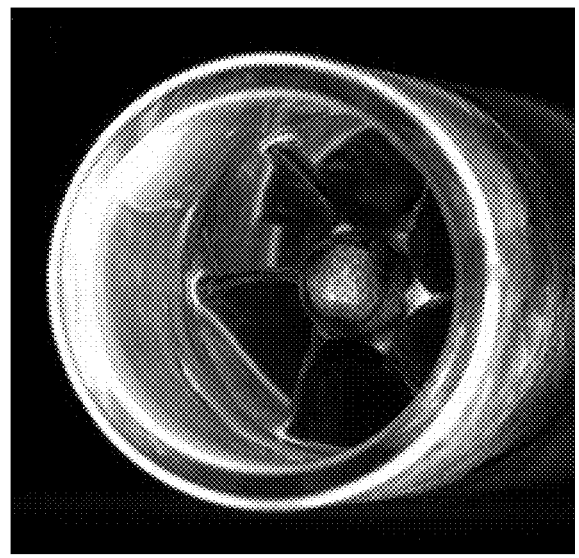
FIG. 6C is a diagram showing the particle adhesion effect on the surfaces of the stator and the wall in the outlet section at a third angle after laser induction.
Figure 6D:
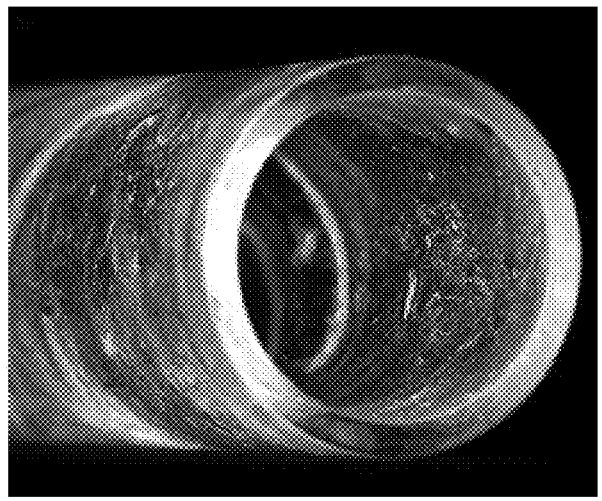
FIG. 6D is a diagram showing the particle adhesion effect on the surfaces of the stator and the wall in the outlet section at a fourth angle after laser induction.

Experimental results are as follows. As shown in FIG. 3, from the adhesion of particles on a component surface observed by photographing after the experiment, it can be seen that the particles show obvious adhesion at locations A, B, and C. FIGS. 4A-4F show the particle adhesion effects on the surface of the rotor at various angles after laser induction, and the adhesion of particles on the surface of the blood pump model rotor is photographed, where, the white points are where the particles aggregate. FIGS. 5A-5D show the particle adhesion effects on the surface of the stator in the inlet section at various angles after laser induction, where, the white points are where the particles aggregate. FIGS. 6A-6D show the particle adhesion effects on the surfaces of the stator and the wall in the outlet section at different angles after laser induction, where, the white points are where the particles aggregate.

It can be seen from the above results that the method of the present invention can locate a location and a structure in a device where platelet adhesion is most likely to occur, thus providing a guiding method for analyzing which local structural deficiencies in the device will cause platelet adhesion and thrombosis.

What is claimed is:

1. A method for an in vitro simulation and an evaluation of platelet adhesion in a blood-contacting medical device, comprising the following steps:
   (1) using a glycerin aqueous solution with a mass percentage concentration of 40% in an extracorporeal circulation circuit to simulate a viscosity and hydrodynamic characteristics of blood, and adding fluorescent particles with a diameter of 3 μm to 5 μm to the glycerin aqueous solution to simulate platelets, to obtain a simulated blood solution;
   (2) after the simulated blood solution circulates in the extracorporeal circulation circuit for 24 h, removing flow passage components of the blood-contacting medical device, and observing a deposition of the fluorescent particles on a blood-contacting surface inside the blood-contacting medical device by naked eyes and photographs; and
   (3) using a laser-induced fluorescence (LIF) technique to apply laser light on the blood-contacting surface to obtain laser-induced fluorescent particles, wherein the blood-contacting surface is deposited with the fluorescent particles, and using a charge-coupled device (CCD) camera imaging method to photograph an aggregation and adhesion of the laser-induced fluorescent particles.

2. The method according to claim 1, wherein in the step (1), the fluorescent particles have a volume percentage concentration of 5% to 30% in the simulated blood solution.

3. The method according to claim 1, wherein the blood-contacting medical device is one selected from the group consisting of an artificial heart, a vascular stent, and a mechanical valve.

4. The method according to claim 3, wherein for the vascular stent and mechanical valve, a traditional rotary pump is configured to achieve a circulation flow of the simulated blood solution in the extracorporeal circulation circuit; and for the artificial heart, the circulation flow of the simulated blood solution in the extracorporeal circulation circuit is achieved directly relying on power of the artificial heart.

5. The method according to claim 1, wherein when the deposition of the fluorescent particles does not occur after 3 days of an experiment, the blood-contacting medical device is removed, and the blood-contacting medical device is determined to have no structural deficiencies, wherein the structural deficiencies lead to the platelet adhesion.

* * * * *